(12) United States Patent
Nagae

(10) Patent No.: US 11,957,434 B2
(45) Date of Patent: Apr. 16, 2024

(54) OBJECT INFORMATION ACQUIRING APPARATUS

(71) Applicant: CANON KABUSHIKI KAISHA, Tokyo (JP)

(72) Inventor: Kenichi Nagae, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 1367 days.

(21) Appl. No.: 16/416,521

(22) Filed: May 20, 2019

(65) Prior Publication Data

US 2019/0274550 A1 Sep. 12, 2019

Related U.S. Application Data

(63) Continuation of application No. 14/129,486, filed as application No. PCT/JP2012/071113 on Aug. 15, 2012, now abandoned.

(30) Foreign Application Priority Data

Aug. 25, 2011 (JP) ................. 2011-183574

(51) Int. Cl.
*A61B 5/00* (2006.01)
*A61B 5/145* (2006.01)
(Continued)

(52) U.S. Cl.
CPC .......... *A61B 5/0095* (2013.01); *A61B 5/0091* (2013.01); *A61B 5/145* (2013.01);
(Continued)

(58) Field of Classification Search
None
See application file for complete search history.

(56) References Cited

U.S. PATENT DOCUMENTS

| 8,396,534 B2 | 3/2013 | Fukutani et al. |
| 2005/0004458 A1 | 1/2005 | Kanayama et al. |

(Continued)

FOREIGN PATENT DOCUMENTS

| CN | 1575770 A | 2/2005 |
| CN | 101371781 A | 2/2009 |

(Continued)

OTHER PUBLICATIONS

K. Yang et al., "Photoacoustic Tomography of Small Animal Brain with a Curved Array Transducer", Journal of Biomedical Optics, 14 (5), pp. 054007-1 through 054007-6 (2009).

(Continued)

*Primary Examiner* — Patricia J Park
(74) *Attorney, Agent, or Firm* — VENABLE LLP

(57) ABSTRACT

An object information acquiring apparatus is used. This apparatus comprises: a light source configured to emit pulsed light of a plurality of wavelengths; a wavelength controller configured to switch the wavelength; a probe configured to receive an acoustic wave generated and propagated in an object subjected to the pulsed light emitted onto the object; a scan controller configured to move the probe within a predetermined scanning range; and an information processor configured to acquire information about the object by using a plurality of electric signals corresponding to the wavelengths of the pulsed light output from the probe at each reception position in the scanning area. The wavelength controller switches the wavelength of the pulsed light before the probe scans the entire scanning area while receiving at each reception position an acoustic wave corresponding to at least one of the wavelengths of the pulsed light.

12 Claims, 15 Drawing Sheets

(51) Int. Cl.
*A61B 8/00* (2006.01)
*A61B 8/08* (2006.01)

(52) U.S. Cl.
CPC ............. *A61B 8/0825* (2013.01); *A61B 8/403* (2013.01); *A61B 8/4281* (2013.01)

(56) References Cited

U.S. PATENT DOCUMENTS

| | | |
|---|---|---|
| 2006/0009693 A1 | 1/2006 | Hanover et al. |
| 2006/0064001 A1 | 3/2006 | Barbour |
| 2008/0221519 A1 | 9/2008 | Schwach et al. |
| 2009/0097512 A1 | 4/2009 | Clowes et al. |
| 2009/0154784 A1 | 6/2009 | Igarashi |
| 2009/0299185 A1 | 12/2009 | Oikawa et al. |
| 2009/0312628 A1 | 12/2009 | Igarashi |
| 2010/0016717 A1 | 1/2010 | Dogra et al. |
| 2010/0094561 A1* | 4/2010 | Masumura ............ A61B 5/0073 73/632 |
| 2010/0220287 A1* | 9/2010 | Sumiya .................... A61B 3/10 351/221 |
| 2011/0058175 A1 | 3/2011 | Suehira |
| 2011/0083511 A1 | 4/2011 | Taki et al. |
| 2011/0098550 A1 | 4/2011 | Yoda |
| 2011/0208035 A1 | 8/2011 | Baba et al. |
| 2011/0307181 A1 | 12/2011 | Nagae |
| 2012/0044785 A1 | 2/2012 | Yoda et al. |
| 2012/0259198 A1 | 10/2012 | Nagae et al. |
| 2013/0118262 A1 | 5/2013 | Naganuma et al. |
| 2014/0051970 A1 | 2/2014 | Ebisawa et al. |

FOREIGN PATENT DOCUMENTS

| | | | |
|---|---|---|---|
| CN | 101601581 A | 12/2009 | |
| JP | 4448189 B2 | 4/2010 | |
| JP | 2010-139510 A | 6/2010 | |
| JP | 2012-231878 A | 11/2012 | |
| WO | 2009/154244 A1 | 12/2009 | |
| WO | 2009/154298 A1 | 12/2009 | |
| WO | WO-2009154244 A1 * | 12/2009 | ........... A61B 5/0059 |
| WO | 2010/009412 A2 | 1/2010 | |
| WO | 2011/096551 A1 | 8/2011 | |
| WO | 03/103500 A1 | 12/2013 | |

OTHER PUBLICATIONS

Office Action dated Dec. 26, 2014, in counterpart P.R. China patent application 201280040520.4 (15 pages).

Office Action dated Feb. 24, 2015, in counterpart Russian patent application 2014111184 (5 pages).

Office Action dated Jul. 16, 2015, in counterpart Russian patent application 2014111184 (13 pages).

E.V. Savvateeva et al., Laser Optoacoustic Biotissue Spectroscopy, Modern Laser-Information and Laser Technology, Written proceedings IPLIT RAN, Intercontact Science, pp. 183-187 (2005) (with English abstract).

Indian Office Action dated May 29, 2019, in counterpart application No. 1833/CHENP/2014 (5 pages).

Office Action dated Jun. 4, 2021, in counterpart In 1833/CHENP/2014 (2 pages).

* cited by examiner

OBJECT INFORMATION ACQUIRING APPARATUS

CROSS-REFERENCE TO RELATED APPLICATIONS

This application is a continuation of U.S. patent application Ser. No. 14/129,486, filed on Dec. 26, 2013, which is a national stage entry of PCT/JP2012/071113, filed Aug. 15, 2012, which claims the benefit of priority from Japanese Application No. 2011-183574, filed Aug. 25, 2011. The contents of the aforementioned applications are incorporated herein by reference in their entireties.

TECHNICAL FIELD

The present invention relates to an object information acquiring apparatus.

BACKGROUND ART

Conventionally, an X-ray mammography apparatus has been known as an image diagnostic apparatus effective in discovering or diagnosing breast cancer. Also, in recent years, the method in which light energy is transmitted through an object, a photoacoustic signal generated as a result of thermal expansion caused by the absorption of the light energy is received, and the inside of the object is imaged based on the photoacoustic signal, has received attention. A photoacoustic signal is an acoustic wave such as an ultrasonic wave. In particular, this signal is also called a photoacoustic wave.

For the reception and processing of a photoacoustic signal, it is preferable to receive the photoacoustic signal and convert it into an electric signal. A photoacoustic signal is generally converted into an electric signal by using a conversion element such as a CMUT (Capacitive Micromachined Ultrasonic Transducer) produced using a piezoelectric element or semiconductor technology. Actually, a probe in which more than one such conversion element is arranged is usually used.

However, it is difficult in terms of cost and yield to manufacture a probe of a size sufficient to simultaneously acquire photoacoustic signals from the entire breast. In order to overcome this problem, PTL 1, for example, describes an ultrasonic diagnostic apparatus that automatically carries out mechanical scanning using an ultrasonic probe to receive photoacoustic signals, and reconstruct a three-dimensional image over a wide examination area.

Meanwhile, the technology for calculating the ratio of present substances of different optical absorption spectra by using photoacoustic signals obtained by the emission of light of a plurality of wavelengths has been studied.

For example, NPL 1 describes a method for calculating oxygen saturation or the like in blood by using a plurality of wavelengths, through focusing on the difference in optical absorption spectra between oxidized hemoglobin and reduced hemoglobin present in blood.

If absorption coefficients ($\mu_a^{\lambda_1}$, and $\mu_a^{\lambda_2}$) corresponding to wavelengths λ1 and λ2 are used in a certain position, oxygen saturation ($SO_2$) is calculated from the expression (1) given below.

[Math. 1]

$$SO_2 = \frac{[HbO_2]}{[HbO_2]+[Hb]} = \frac{\mu_a^{\lambda_2}\varepsilon_{Hb}^{\lambda_1} - \mu_a^{\lambda_1}\varepsilon_{Hb}^{\lambda_2}}{\mu_a^{\lambda_1}\Delta\varepsilon_{Hb}^{\lambda_2} - \mu_a^{\lambda_2}\Delta\varepsilon_{Hb}^{\lambda_1}} \quad (1)$$

Here, $[HbO_2]$ is the concentration of oxidized hemoglobin and [Hb] is the concentration of reduced hemoglobin. Symbols $\varepsilon_{Hb}^{\lambda_1}$ and $\varepsilon_{Hb}^{\lambda_2}$ are molar absorption coefficients of reduced hemoglobin at wavelengths λ1 and λ2 respectively. Symbols $\Delta\varepsilon_{Hb}^{\lambda_1}$ and $\Delta\varepsilon_{Hb}^{\lambda_2}$ are values found by subtracting the molar absorption coefficients of reduced hemoglobin from the molar absorption coefficients of oxidized hemoglobin at wavelengths λ1 and λ2 respectively.

Also, PTL 2 describes an apparatus for measuring glucose concentration by emitting two wavelengths.

CITATION LIST

Patent Literature

PTL 1: Japanese Patent No. 4448189
PTL 2: Japanese Patent Application Laid-Open No. 2010-139510

Non Patent Literature

NPL 1: Journal of Biomedical Optics 14(5), 054007

SUMMARY OF INVENTION

Technical Problem

However, where mechanical scanning is carried out with a probe such that a plurality of wavelengths are emitted onto an observation area of a certain object and photoacoustic signals corresponding to the wavelengths are acquired, the problem may occur that the object moves during scanning.

Imaging time (photoacoustic wave reception time) required to acquire photoacoustic signals from an area (240 mm×180 mm) equal to a panel used in general mammography is calculated in the manner described below. As an example, it is assumed that the element size is 2 square mms, the number of reception CHs is 500 CHs, the repetition frequency of light emission is 10 Hz, and the average is calculated from 256 measurements in order to improve the reception signal SN ratio. In this case, by simple arithmetic, (240×180×256)÷(2×2×500×10)=552.96 (secs), that is, an imaging time of about 9 min is required in order to acquire photoacoustic signals corresponding to one wavelength.

As described above, to calculate, for example, oxygen saturation, absorption coefficients corresponding to a plurality of wavelengths at focused points are used. However, if there is a time difference of about 9 mins between the point in time that a photoacoustic signal at a focused point is acquired using wavelength λ1 and the point in time that a photoacoustic signal at the focused point is acquired using wavelength λ2, there is a high possibility of displacement of an object, especially, of a living biological object.

In order to calculate oxygen saturation or the like at a certain focused point, absorption coefficients corresponding to wavelengths λ1 and λ2 at the focused point have to be used. If there is displacement due to the time difference between the points in time that data corresponding to wavelength λ1 is acquired (the point in time that a photoacoustic wave is received) and data corresponding to wavelength λ2 is acquired (the point in time that a photoacoustic wave is received), it means that oxygen saturation is consequently calculated using absorption coefficients corresponding to different positions. This leads to error in the calculation result, and degradation in reliability and accuracy.

The present invention has been proposed in view of the foregoing problems. It is accordingly the object of the present invention to provide a technology to prevent an object information acquiring apparatus, which acquires photoacoustic signals by using light of a plurality of wavelengths, from being affected by error due to object movement.

Solution to Problem

The present invention provides an object information acquiring apparatus, comprising:
  a light source configured to emit pulsed light of a plurality of wavelengths;
  a wavelength controller configured to switch the wavelength of the pulsed light;
  a probe configured to receive an acoustic wave generated and propagated in an object subjected to the pulsed light emitted onto the object;
  a scan controller configured to move the probe within a predetermined scanning range; and
  an information processor configured to acquire information about the object by using a plurality of electric signals corresponding to the wavelengths of the pulsed light output from the probe at each reception position in the scanning area;
  wherein the wavelength controller switches the wavelength of the pulsed light before the probe scans the entire scanning area while receiving at each reception position an acoustic wave corresponding to at least one of the wavelengths of the pulsed light.

Advantageous Effects of Invention

The present invention is able to provide a technology to prevent an object information acquiring apparatus, which acquires photo acoustic signals by using light of a plurality of wavelengths, from being affected by error due to object movement.

Further features of the present invention will become apparent from the following description of exemplary embodiments with reference to the attached drawings.

DESCRIPTION OF EMBODIMENTS

Referring to the accompanying drawings, preferred embodiments of the present invention will be described below.

An object information acquiring apparatus is an apparatus that uses a photoacoustic effect in which an acoustic wave (typically ultrasonic wave) generated in an object by emitting light (electromagnetic wave) onto the object and propagated in this object is received and information about the object is acquired as image data. The acoustic wave generated by photoacoustic effect is also called a photoacoustic wave. Examples of object information include the initial acoustic pressure of the acoustic wave, the density of light energy absorbed, absorption coefficient, information reflecting the concentrations of substances composing the tissues in the object, and other information, all of which may be derived from the reception signals of acoustic waves. The concentrations of substances may be, for example, oxygen saturation, oxyhemoglobin/deoxyhemoglobin concentration, or glucose concentration. Additionally, object information may be acquired as numerical or image data indicating distribution information at each place (i.e., each target point) in an object. That is, object information may be acquired as image data indicating distribution information reflecting, for example, oxygen saturation distribution in an object.

The outline of a photoacoustic signal acquiring operation will now be explained with reference to FIGS. 14 and 15.

Figure 14:
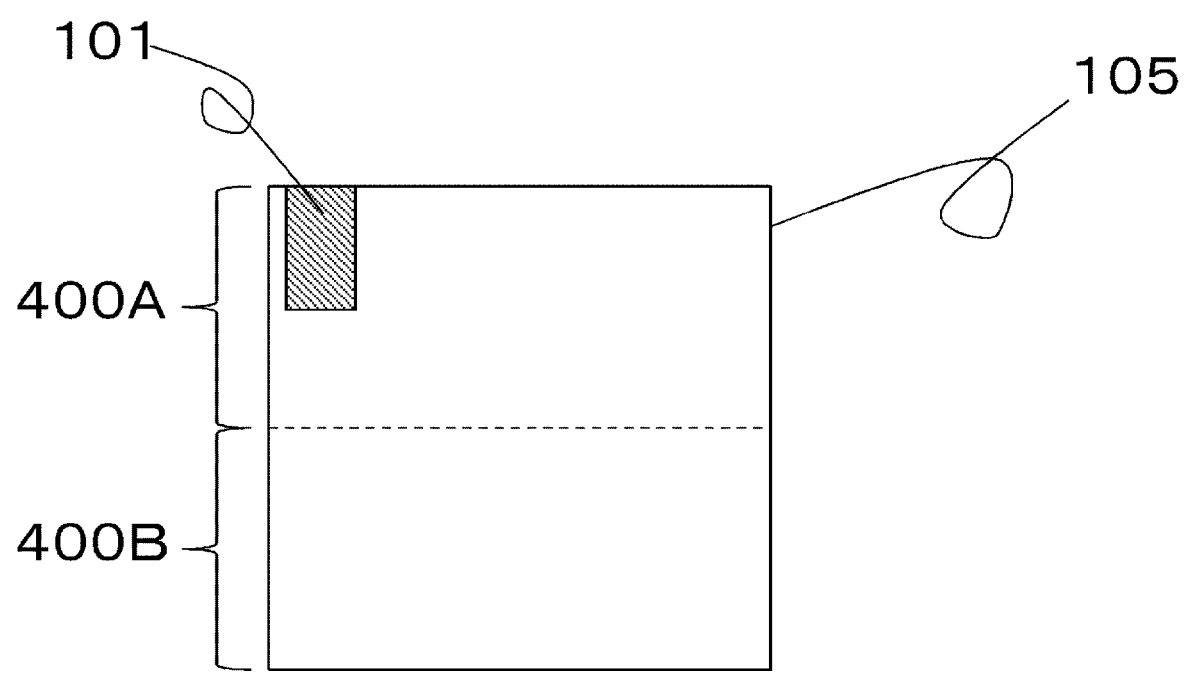
FIG. 14 is a diagram schematically showing a data acquisition range according to the present invention.

FIG. 14 is a diagram schematically showing a data acquisition range according to the present invention. In the present invention, "the data acquisition range" refers to a predetermined scanning range that includes a plurality of reception positions at which a probe receives acoustic waves, and that is scanned in order that the probe receive a plurality of acoustic waves. This predetermined data acquisition range may be a range determined in advance or may be a range specified by a user every time. While scanning within this data acquisition range, the probe receives acoustic waves, thereby making it possible to acquire, as image data, three-dimensional object information, such as oxygen saturation distribution in an object. The probe 101 moves within the data acquisition range 105 and receives photoacoustic waves. In the description below, such photoacoustic waves detected by the probe are called photoacoustic signals.

Figure 15A:
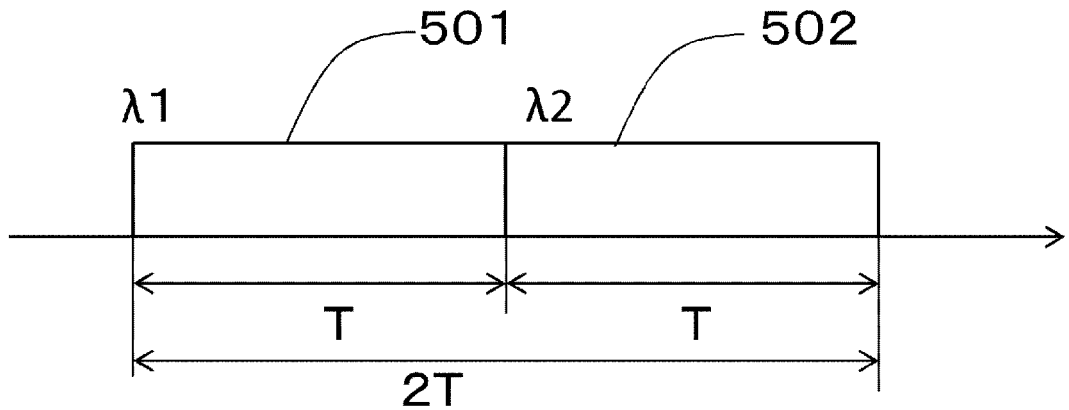
FIGS. 15A to 15C are time charts of data acquisition according to the existing or present invention.

Here, it is assumed that photoacoustic signals corresponding to pulsed light of two different wavelengths, λ1 and λ2, is acquired over the data acquisition range 105. Where the present invention is not used, it is assumed that the operation is performed such that a photoacoustic signal corresponding to pulsed light of wavelength λ1 is captured over the entire area of the data acquisition range 105, then, wavelength switching is carried out, and a photoacoustic signal corresponding to pulsed light of wavelength λ2 is acquired over the entire data acquisition range 105. As shown in FIG. 15A, the operation is composed of time 501 taken to acquire a photoacoustic signal corresponding to pulsed light of wavelength λ1 and time 502 taken to acquire a photoacoustic signal corresponding to pulsed light of wavelength λ2. If the time required for the probe 101 to scan over the entire data acquisition range 105 is represented by T, a time of 2T is required in total. Additionally, there is an average difference of T between the times required to acquire photoacoustic signals corresponding to the different wavelengths.

Figure 15B:
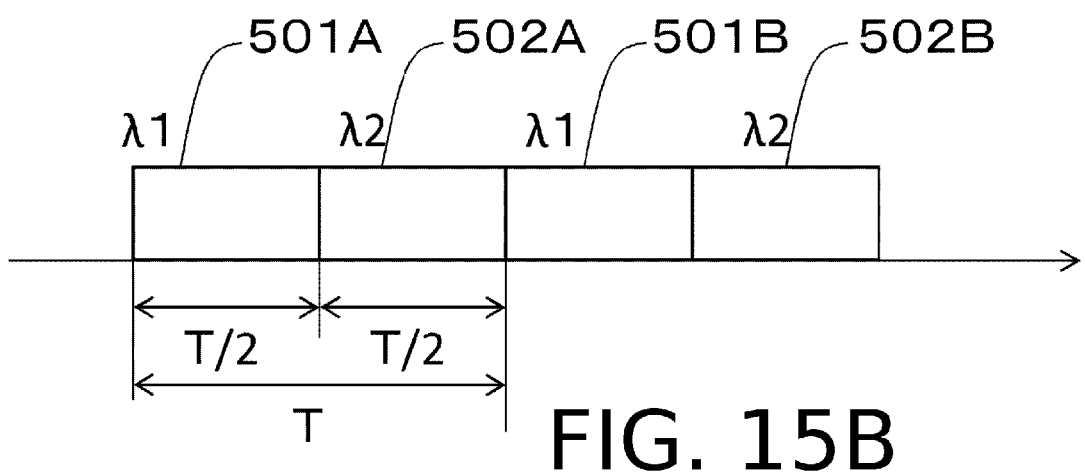

Next will be described data acquisition where the present invention is used. The data acquisition range 105 is divided into a partial data acquisition range 400A and a partial data acquisition range 400B, which are partial areas. Order of data acquisition is shown in FIG. 15B. That is, the following procedure may be performed: a photoacoustic signal corresponding to pulsed light of wavelength λ1 (a first wavelength) is first acquired (501A) in the partial data acquisition range 400A, then wavelength switching is carried out, and a photoacoustic signal corresponding to pulsed light of wavelength λ2 (a second wavelength) is acquired (502A) in the partial data acquisition range 400A; next, wavelength switching is again carried out, a photoacoustic signal corresponding to pulsed light of wavelength λ1 is acquired (501B) in the partial data acquisition range 400B, then, wavelength switching is carried out, and a photoacoustic signal corresponding to pulsed light of wavelength λ2 is acquired (502B) in the partial data acquisition range 400B. If the time required for the probe 101 to scan over the entire data acquisition range 105 is represented by T, the total time required is 2T, which is the same as the above. However, the average difference between the times required to acquire photoacoustic signals corresponding to the different wavelengths decreases to T/2.

That is, before a photoacoustic signal generated by emission of pulsed light of one of two wavelengths is acquired over the entire acquisition range 105, the wavelength is switched to the other, and a photoacoustic signal is acquired using this wavelength. This means that before completing a scan of the entire data acquisition range (scanning range) while receiving a photoacoustic wave corresponding to pulsed light of one wavelength at each reception position, switching between the wavelengths of the pulsed light is carried out. This makes it possible to reduce the difference between the times required to acquire photoacoustic signals corresponding to the different wavelengths. In this case, wavelength switching is carried out three times.

Figure 15C:
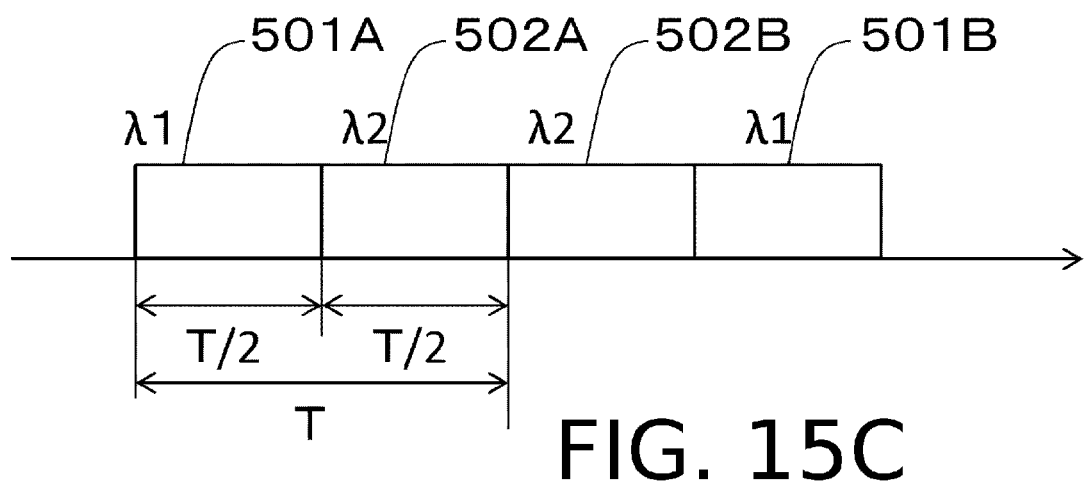

In addition, there may be a case as shown in FIG. 15C. That is, the following procedure may be performed: a photoacoustic signal corresponding to pulsed light of wavelength λ1 is first acquired (501A) in a partial data acquisition range 400A, then wavelength switching is carried out, and a photoacoustic signal corresponding to pulsed light of wavelength λ2 is acquired (502A) in the partial data acquisition range 400A; subsequently, a photoacoustic signal corresponding to pulsed light of wavelength λ2 is acquired (502B) in the partial data acquisition range 400B, then, wavelength switching is carried out, and a photoacoustic signal corresponding to pulsed light of wavelength λ1 is acquired (501B) in the partial data acquisition range 400B. In this case also, the difference between the times required to acquire photoacoustic signals corresponding to the different wavelengths can be reduced just as in the above. In this case, wavelength switching is carried out two times.

If the entire data acquisition area is divided into an M number of partial data acquisition ranges (partial areas) (M≥2) in a case where photoacoustic signals are acquired with different wavelengths of N types by using the present invention, the minimum value for the number of wavelength switching times is (N−1)×M. In the preceding example, since two types of wavelength are used and the entire data acquisition area is divided into two partial data acquisition ranges, the minimum number of times is (2−1)×2=2.

Incidentally, where the present invention is not used, in which the entire data acquisition range is scanned with one wavelength and then the wavelength is switched to the other, the number of wavelength switching times is (N−1).

That is, before all data (acoustic waves) are acquired at all reception positions within a data acquisition range by the emission of pulsed light of different wavelengths of N types, the wavelength is switched (N−1)×M times, thereby reducing the difference between the times required to acquire photoacoustic signals corresponding to the different wavelengths. That is to say, error due to movement of an object, which accompanies the passage of time, can be prevented.

First Embodiment

An embodiment of a biological information processing apparatus according to the present invention will be described in detail below with reference to the drawings.

First, the outline and operation of a system according to the present embodiment will be explained and then a data acquiring operation will be described.

Figure 6C:
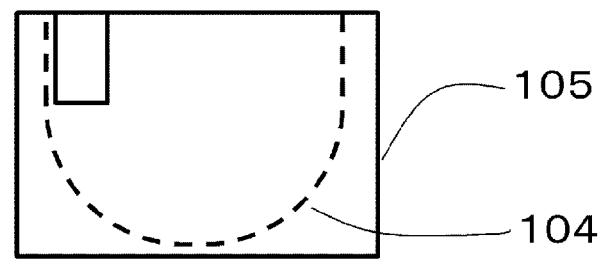
FIGS. 6A to 6C are diagrams showing the configuration of an ultrasonic diagnostic apparatus according to the first embodiment.
Figure 6A:
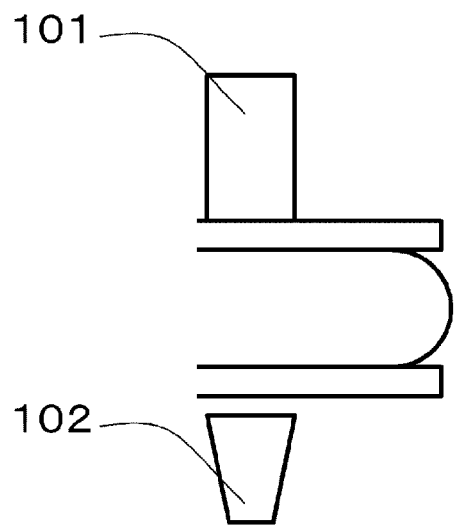
Figure 6B:
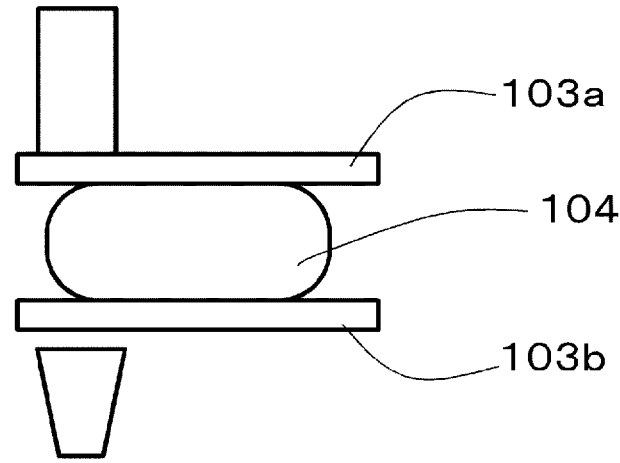

FIG. 6 is a diagram of an ultrasonic diagnostic apparatus according to the first embodiment of the present invention, and shows the configuration of parts around objects. Each of FIGS. 6A and 6B is a cross-sectional view of the apparatus as viewed from a direction perpendicular to the direction in which the object is compressed. FIG. 6C is a plan view of a holding plate as viewed from a direction in which the object is compressed.

Each object (a breast in this embodiment) 104 is sandwiched and held between two holding plates 103 (103a and 103b). A probe 101 is installed on the opposite side of the holding plate 103a to the breast 104. A light emission unit 102 is installed at the opposite side of the holding plate 103b to the breast 104. The probe 101 and light emission unit 102 move in a data acquisition range 105, as shown by a change from FIG. 6A to FIG. 6B.

The object is not a component of any part of the object information acquiring apparatus of the present invention. However, its explanation is as follows: if an object information acquiring apparatus is used for diagnosis of malignant tumor, blood vessel disease, blood sugar level, or the like in a human being or animal or for follow-up to chemical treatment, a site other than a breast, such as a finger, hand or foot of a human being or animal may be assumed to be an object.

Figure 7:
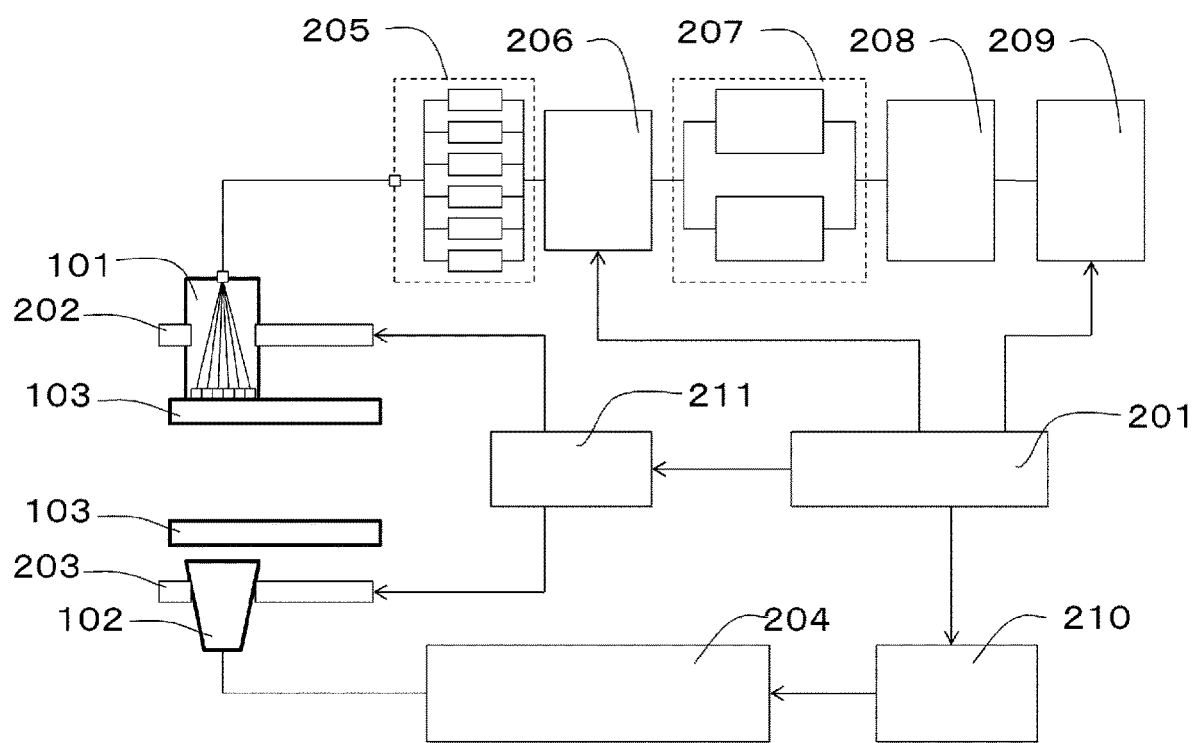
FIG. 7 is a schematic view of a system according to the present invention.

FIG. 7 is a diagram showing the outline of a system of the present embodiment. A laser light source 204 generates pulsed light (typically, 100 nsec or shorter) of wavelength (typically 700 nm to approximately 1100 nm) close to near-infrared, according to a timing control signal from a system controller 201 and a wavelength control signal from a laser wavelength controller 210. After transmission along an optical transmission path, these pulsed light are transmitted through the holding plate 103 (not shown) from the light emission unit 102 and emitted onto an object (not shown). Consequently, a light absorber in the object absorbs the pulsed light and generates acoustic waves. In the present invention, light refers to electromagnetic waves including visible and infrared rays. According to the constituent to be measured, a specific wavelength may be selected. The laser wavelength controller serves as a wavelength controller according to the present invention, and the laser light source serves as a light source according to the present invention.

The probe 101 has a plurality of conversion elements. Using these conversion elements, the probe receives photoacoustic waves passed through the holding plate 103 and converts them into electric signals (reception signals). A reception circuit system 205 subjects reception signals output from the probe 101 to sampling and amplifying processes and converts these signals into digital signals (digitized reception signals).

Using data acquisition range information specified by the system controller 201, a scan controller 211 controls the probe scanning mechanism 202 and the emission system scanning mechanism 203 and moves the probe 101 and light emission unit 102. Then, light emission and photoacoustic signal reception as described above are carried out repeatedly.

A reconstruction block 206 performs an image reconstruction process using information about probe position and so on input from the system controller 201 and using digital signals input from the reception circuit system 205. This image reconstruction is a process for calculating initial acoustic pressure distribution p(r) of photoacoustic waves in an object by using FBP (Filtered Back Projection) or the like, expressed by, for example, the formula (2) given below.

[Math. 2]

$$p(r) = -\frac{1}{2\pi} \int_{S_0} \int \frac{dS_0}{r_0^2} \left[ t \frac{\partial p_d(r_0, t)}{\partial t} + 2p_d(r_0, t) \right]_{t=|r-r_0|/c} \quad (2)$$

wherein, $dS_0$ is the size of a detector, $S_0$ is the size of an aperture used for reconstruction, each $P_d$ ($r_0$, t) is a signal received by the corresponding conversion element, $r_0$ is the position of the corresponding conversion element, and t is a reception time.

For each wavelength, a reconstruction data storing unit 207 holds the initial acoustic pressure distributions reconstructed from different wavelengths.

From this reconstruction data storing unit 207, a multi-wavelength composing unit 208 receives initial acoustic pressure distribution data reconstructed from the different wavelengths, and performs computation, thereby calculating object information such as oxygen saturation. Glucose concentration can also be calculated by appropriately controlling a plurality of different wavelengths. An image display unit 209 displays an image by its being controlled by the system controller 201. Examples of an image displayed may include, for example: an image showing the initial acoustic distribution or absorption coefficient distribution calculated from photoacoustic signals acquired using one wavelength; and oxygen saturation calculated by the multi-wavelength composing unit 208.

The process performed from the re construction block to the multi-wavelength composing unit 208 corresponds to the process performed by the information processor according to the present invention.

Next, the acquisition of photoacoustic signals by using a plurality of wavelengths will be explained with reference to the drawings.

Figure 1:
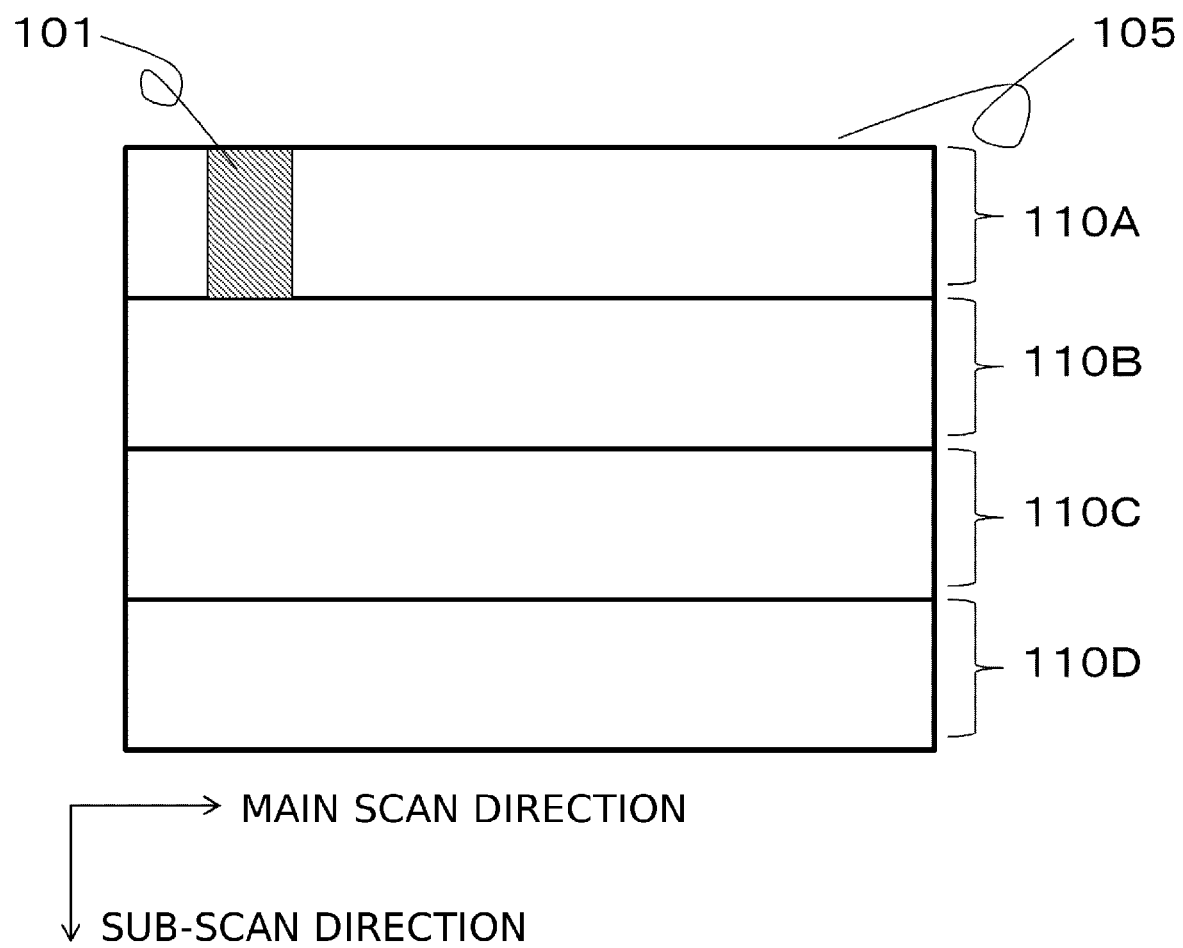
FIG. 1 is a diagram schematically showing the concept of data acquisition using a plurality of wavelengths.

FIG. 1 schematically shows the outline of data acquisition. With reference to this drawing, a description is given of the operation of acquiring photoacoustic signals by using a plurality of wavelengths.

The probe 101 with the conversion elements moves, thereby acquiring data (acoustic waves) at respective positions within the data acquisition range 105. At this time, the probe moves in the data acquisition range such that the probe 101 moves in main scan and sub-scan directions a plurality of times. If it is assumed that the probe moves in the manner of a Raster scan, the main scan direction refers to the direction of movement along a scan line, that is, the direction in which the probe moves while receiving an acoustic signal at each reception position. The sub-scan direction refers to the direction of movement between the scan lines, that is, the direction intersecting (typically, orthogonal to) the main scan direction. It is assumed that each partial data acquisition range, which is acquired by one movement in the main scan direction, is assigned to 110A, 110B, 110C, and 110D. In the present embodiment, the partial data acquisition ranges are areas into which the data acquisition range, i.e., the scanning range, is divided in the sub-scanning direction. Additionally, each of the partial data acquisition ranges 110A, 110B, 110C, and 110D is a range corresponding to a scanning orbit followed by the probe moving in the main scan direction within the data acquisition range while receiving an acoustic wave at each reception position.

It is assumed that photoacoustic signals generated by the emissions of pulsed light of two different wavelengths are acquired over the data acquisition range 105. For example, where photoacoustic signals are acquired by the emissions of two wavelengths ($\lambda 1$ and $\lambda 2$), it is necessary to acquire photoacoustic signals by emitting the wavelengths of the two types to the four partial data acquisition ranges.

Figure 2:
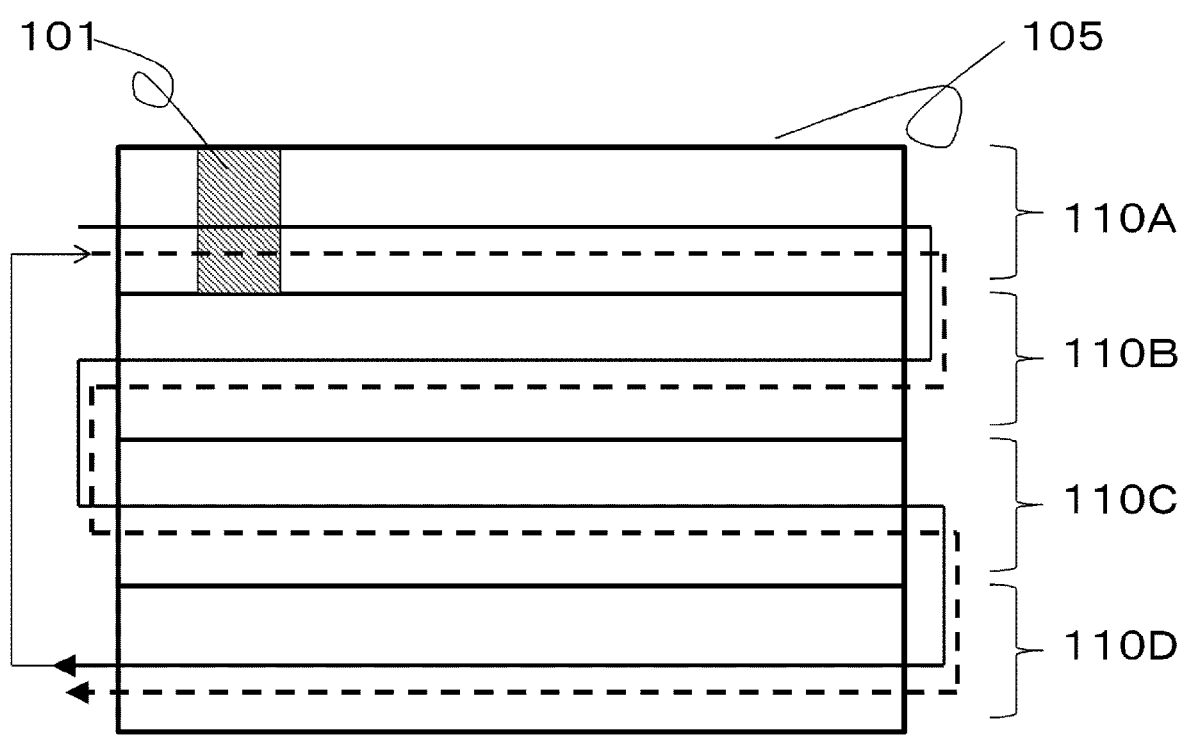
FIG. 2 is a diagram schematically showing probe movement that does not use the present invention.

As a comparative example, an operation in which the present invention is not used is explained with reference to FIG. 2.

First, a probe acquires data (acoustic waves) (indicated by the solid-line arrow) by moving within the data acquisition range 105 while emitting pulsed light of wavelength $\lambda 1$. Then, the wavelength of the pulsed light is switched to $\lambda 2$, and the probe is moved (indicated by the broken-line arrow) within the data acquisition range 105.

Figure 3:
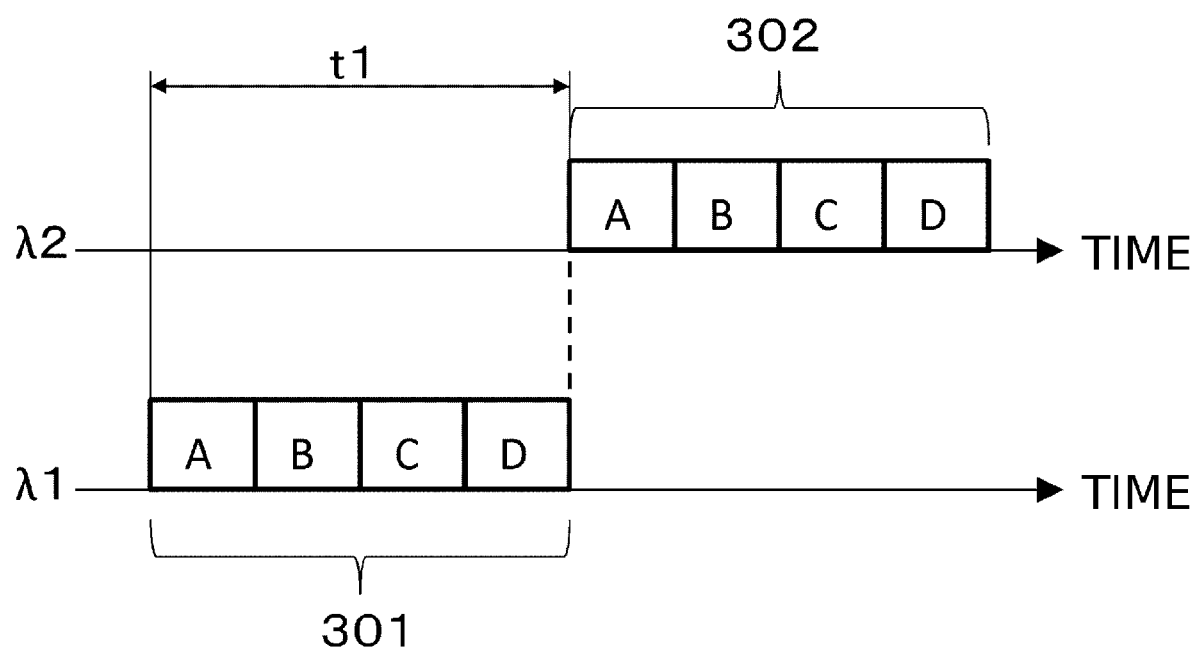
FIG. 3 is a time chart showing data acquisition that does not use the present invention.

FIG. 3 is a time chart showing the partial data acquisition ranges and emitted wavelengths in the cases where such movements are carried out. The symbols A, B, C, and D (301) on the axis represented by $\lambda 1$ in the drawing indicate timings of acquisition of the respective photoacoustic signals in the partial data acquisition ranges (110A, 110B, 110C, and 110D) within which pulsed light of wavelength $\lambda 1$ has been emitted. Additionally, A, B, C, and D (302) represent the timings of the acquisition of the respective photoacoustic signals in the partial data acquisition ranges (110A, 110B, 110C, and 110D) within which pulsed light of wavelength $\lambda 2$ has been emitted.

In the moving method described above, by emitting one of the two different wavelengths, all photoacoustic signals are acquired from the data acquisition range 105.

Where such probe scanning is carried out, the acquisition interval between the respective photoacoustic signals relating to wavelengths $\lambda 1$ and $\lambda 2$ within the same partial data acquisition range (e.g., 110A) is indicated by t1.

Figure 4:
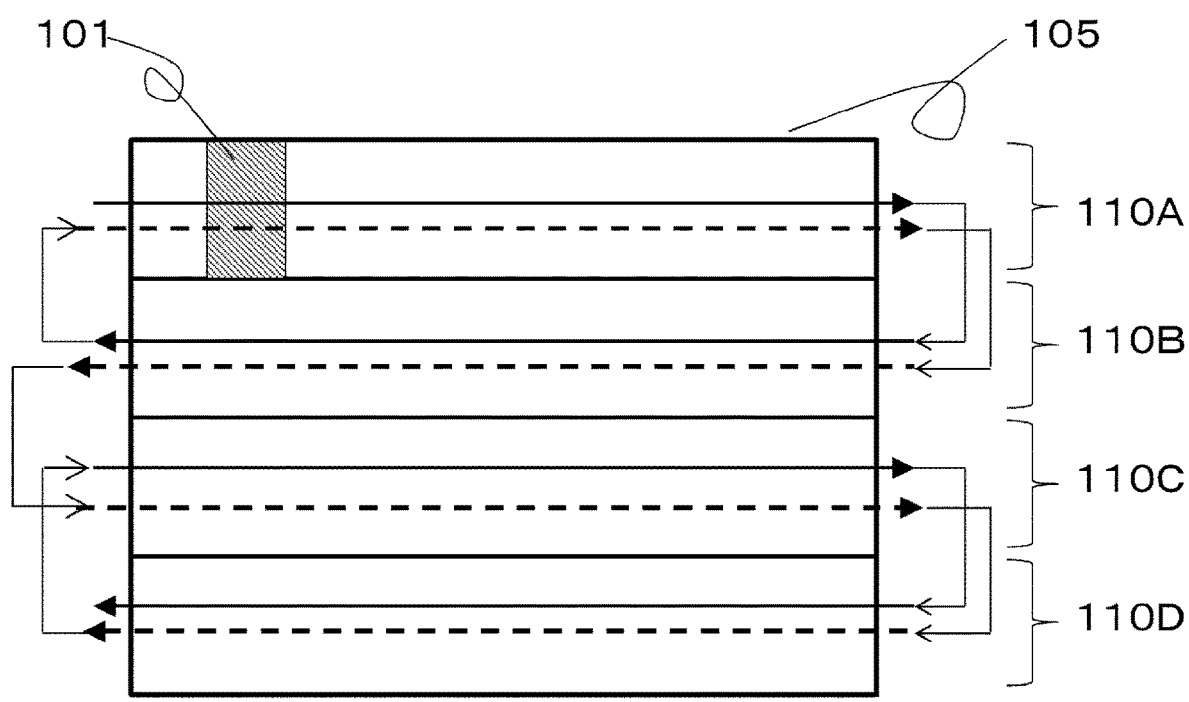
FIG. 4 is a diagram schematically showing probe movement according to the present invention.

FIG. 4 illustrates a data acquiring operation in which the present invention is used.

First, a wavelength control signal is transmitted to the laser light source 204 from the laser wavelength controller 210 and the wavelength is set to λ1. A timing control signal for laser emission is transmitted from the system controller 201 and thereby the laser light source 204 generates pulsed light of wavelength λ1. In response to a control signal from the scan controller 211, the probe 101 and light emission unit 102 are moved in the main scan direction. In such a manner, photoacoustic signals corresponding to pulsed light of wavelength λ1 are acquired (the solid-line arrow in 110A) within the partial data acquisition range 110A. Subsequently, the probe 101 and light emission unit 102 are shifted to the sub-scan direction and moved within the partial data acquisition range 101B. Then, while the probe 101 and light emission unit 102 are moved in the main scan direction within the partial data acquisition range 110B, light emission and data acquisition are carried out (the solid-line arrow in 110B). Thus, data in the partial data acquisition ranges 110A and 110B are acquired.

Next, a wavelength control signal is transmitted to the laser light source 204 from the laser wavelength controller 210 and the wavelength is set to λ2. Thereafter, photoacoustic signals corresponding to pulsed light of wavelength λ2 are acquired in the partial data acquisition ranges 110A, 110B, 110C, and 110D (broken-line arrows in 110A to 110D).

Subsequently, a wavelength control signal is again transmitted to the laser light source 204 from the laser wavelength controller 210, and the wavelength is set to λ1. Then, photoacoustic signals corresponding to pulsed light of wavelength λ1 are acquired within the data acquisition ranges 110C and 110D.

Figure 5:
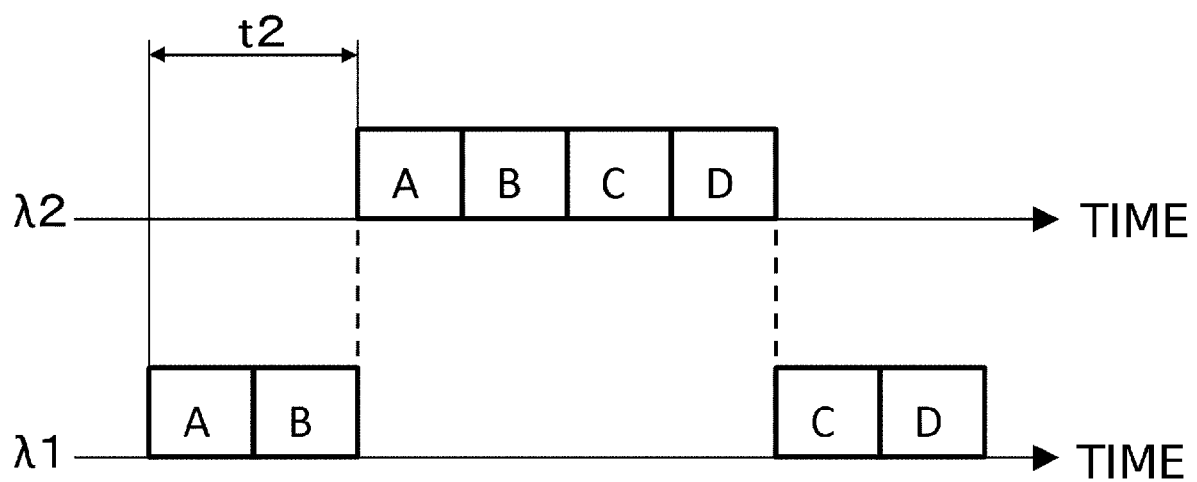
FIG. 5 is a time chart showing data acquisition according to the present invention.

FIG. 5 is a time chart showing the partial data acquisition ranges and emitted wavelengths in a case where such movements have been performed. Each of the two dotted-lines between the axes λ1 and λ2 indicates that wavelength switching has been carried out. That is, wavelength switching has been carried out two times. Specifically, electric signals corresponding to the wavelengths of the pulsed light have been output from the probe at their respective reception positions.

In probe scanning in the present embodiment, before all photoacoustic signals are acquired from within the data acquisition range 105 by emitting pulsed light of one of the two different wavelengths (for example, λ1), the wavelength of pulsed light is switched. Also, at the points in time that the second and sixth movements in the main scan direction of the movements (eight times) in the main scan direction have been completed, the wavelength of pulsed light generated by the laser light source 204 is switched.

In probe scanning in the present embodiment, the acquisition interval between the respective photoacoustic signals relating to wavelengths λ1 and λ2 within the same partial data acquisition range 110A is indicated by t2. As described above, this acquisition interval is shorter than the case where a photoacoustic signal corresponding to the emission of pulsed light of wavelength λ1 and subsequently a photoacoustic signal corresponding to the emission of pulsed light of wavelength λ2 are acquired within the entire data acquisition range 105. Accordingly, in the present embodiment, interval t2 is half of t1.

Therefore, according to the present embodiment, error due to movement of an object, which accompanies the passage of time, can be prevented. Accordingly, when oxygen saturation and so on are calculated using reception signals corresponding to the two wavelengths (λ1 and λ2), error resulting from displacement is prevented, and a highly reliable, highly accurate image can be composed. In the present embodiment, two initial acoustic pressure distributions corresponding to the two wavelengths are obtained in advance, and then oxygen saturation distribution is obtained. However, without obtaining these initial acoustic pressure distributions, oxygen saturation and so on can be obtained using electric signals (reception signals) output from the probe when photoacoustic waves are received.

Also, in the present embodiment, the acquisition of data within each partial data acquisition range is completed by one movement in the main scan direction. However, in order to obtain a required signal SN ratio, movement in the main scan direction may be carried out a plurality of times while pulsed light of the same wavelength is emitted. For example, even by exerting control such that movement in the sub-scan direction is carried out after one forward and backward movement in the main scan direction, the same advantageous effect of the present invention can be obtained.

Second Embodiment

Figure 8A:
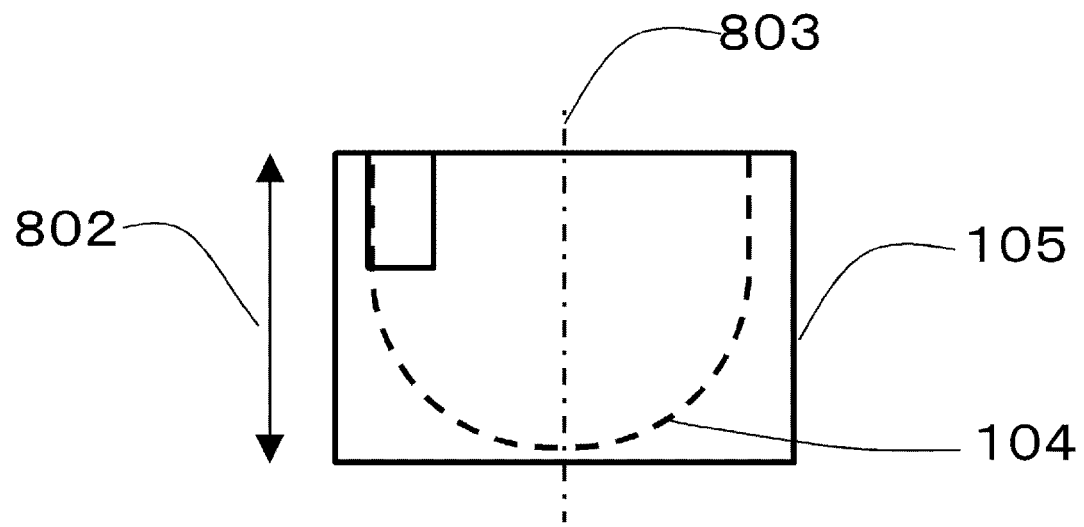
FIGS. 8A and 8B are diagrams showing the configuration of an ultrasonic diagnostic apparatus according to the second embodiment.
Figure 8B:
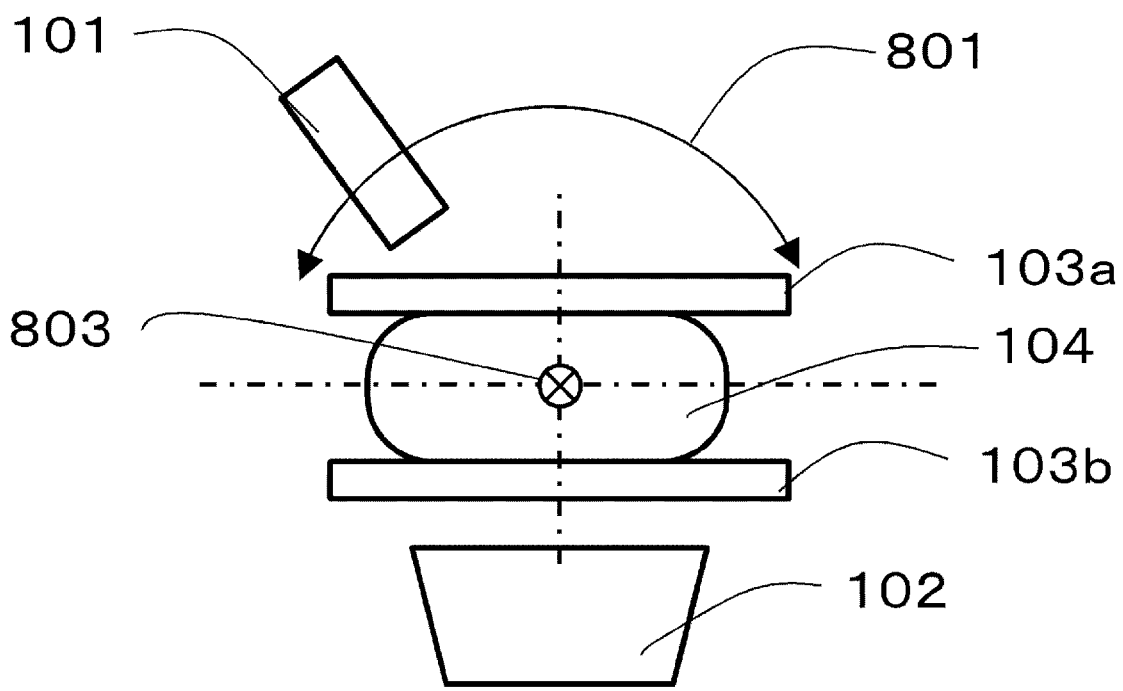

FIG. 8 shows diagrams of an ultrasonic diagnostic apparatus according to the second embodiment of the present invention, and shows the configuration of parts around an object. FIG. 8B is a cross-sectional view of the apparatus as viewed from a direction perpendicular to the direction in which the object is compressed, and FIG. 8A is a plan view of a holding plate as viewed from a direction in which the object is compressed.

An object (a breast in the present embodiment) 104 is sandwiched and held between two holding plates 103 (103a and 103b). A probe 101 is installed at the opposite side of the holding plate 103a to the breast 104. A light emission unit 102 is installed at the opposite side of the holding plate 103b to the breast 104. The probe 101 and light emission unit 102 are moved so as to acquire data within a data acquisition range 105.

The probe 101 moves in a circular direction 801, as a main scan direction, around an axis 803 in the object, and moves in a direction 802, as a sub-scan direction, substantially perpendicular to the main scan direction.

In order to receive acoustic waves transmitted through the holding plates 103, a medium (e.g. water or caster oil) that transmits ultrasonic waves is injected between the probe 101 and holding plates 103.

Since the outline of the system and the flow of data processing are the same as those in the first embodiment, explanation thereof is omitted, and acquisition of photoacoustic signals by using a plurality of wavelengths will be explained with reference to the drawings.

Figure 9:
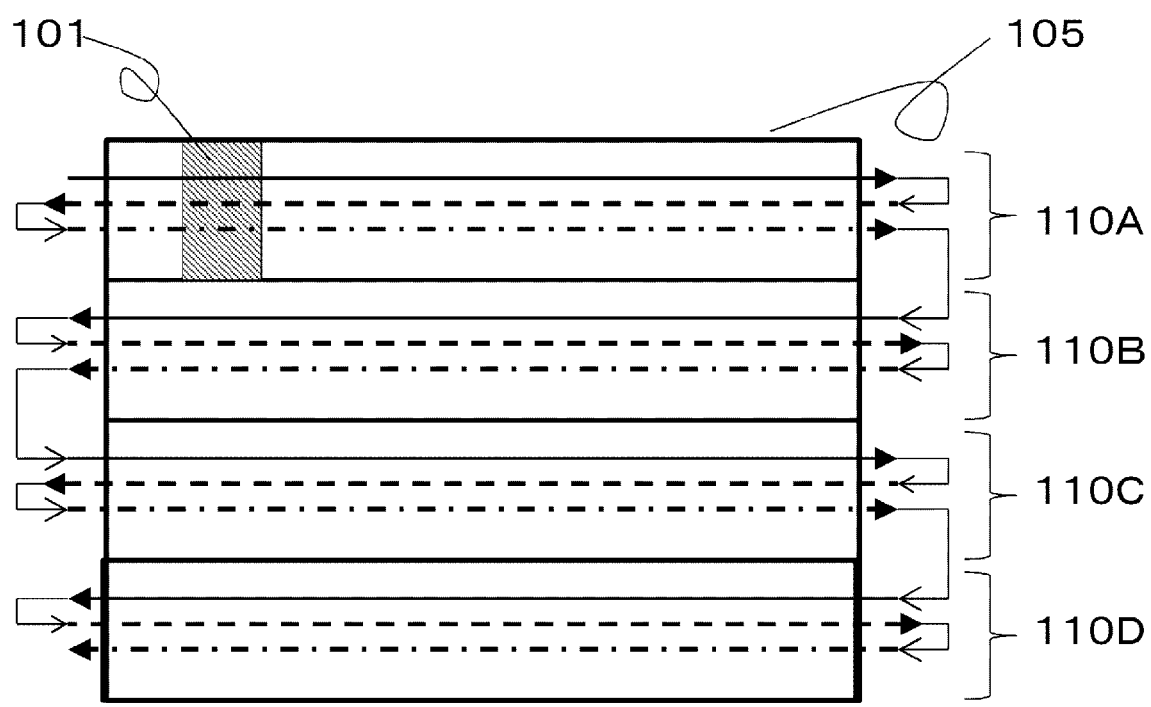
FIG. 9 is a diagram schematically showing probe movement according to the second embodiment.

FIG. 9 illustrates a data acquiring operation that is performed in the present embodiment. The main scan direction is a circular direction around the axis 803, as described above. However, here, a two-dimensional drawing in which the circular directions are developed in plane is used for ease of explanation.

In the present embodiment, a description will be given of a case where three wavelengths are used.

First, a wavelength is set to λ1 and the probe 101 is moved in the main scan direction, thereby acquiring a photoacoustic signal corresponding to pulsed light of wavelength λ1 (solid-line arrow) within a partial data acquisition range 110A. Subsequently, the wavelength is switched to λ2, and a photoacoustic signal corresponding to pulsed light of wavelength λ2 is acquired (broken-line arrow) in the partial data acquisition range 110A. Further, the wavelength is switched to λ3 and, then, a photoacoustic signal corresponding to pulsed light of wavelength λ3 is acquired (chain-line arrow) in the partial data acquisition range 110A. Thereafter, the probe shifts to the sub-scan direction, and acquires data within the partial data acquisition range 110B. By repeating such an operation, data up to a partial data acquisition range 110D may be acquired.

As described above, before shifting to the sub-scan direction, movement in the main scan direction is carried out (at least twice, specifically three times in the present embodiment), and control for wavelength change is exerted at the time point in time that one of the movements in the main scan direction has been completed.

Figure 10:
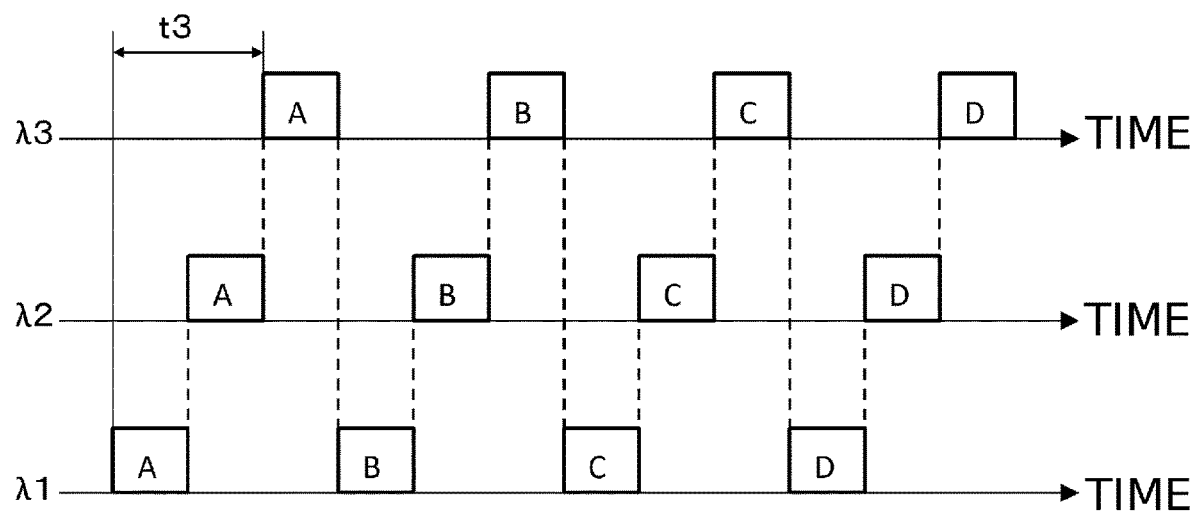
FIG. 10 is a time chart showing data acquisition according to the second embodiment.

FIG. 10 is a time chart showing the partial data acquisition ranges and emitted wavelengths, according to the present embodiment. In probe scanning in the present embodiment, the acquisition interval between the respective photoacoustic signals relating to wavelengths λ1 and λ3 within the same partial data acquisition range 110A, is indicated by t3. This acquisition interval is notably shorter than the case where, after photoacoustic signals corresponding to the emission of pulsed light of wavelength λ1 are acquired in the entire data acquisition range 105, photoacoustic signals corresponding to emission of pulsed light of the wavelength λ2 and photoacoustic signals corresponding to emission of pulsed light of the wavelength λ3 are acquired. In the present embodiment, the time difference is reduced to ¼ of the case in which the present invention is not used.

According to the present embodiment, wavelength switching and movement in the main scan direction are carried a plurality of times before shifting to the sub-scan direction. Therefore, acquisition intervals between the photoacoustic signals corresponding to different wavelengths within the same partial data acquisition range can be further shortened. That is, error due to movement of an object, which accompanies the passage of time, can be further reduced.

Therefore, by use of data reconstructed from photoacoustic signals obtained from the wavelengths (λ1, λ2, and λ3), error resulting from displacement is further reduced when oxygen saturation and so on are calculated in the multi-wavelength composing unit. Accordingly, a more reliable, highly accurate image can be composed.

In the present embodiment, the main scan direction is specified as circular direction around the axis. However, even where the probe is used for two-dimensional scanning as in spatial arrangement of the first embodiment, the advantageous effects of the present invention can be obtained.

Third Embodiment

Figure 11A:
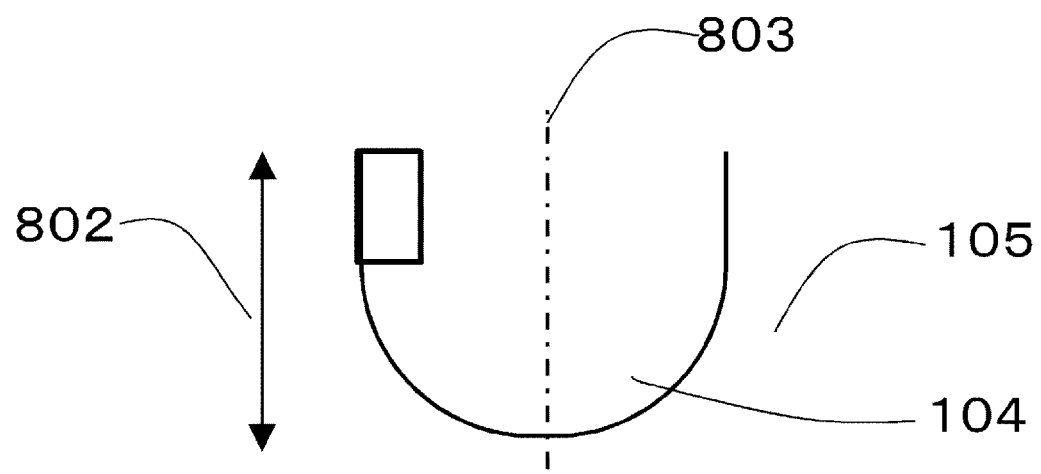
FIGS. 11A and 11B are diagrams showing the configuration of an ultrasonic diagnostic apparatus according to the third embodiment.
Figure 11B:
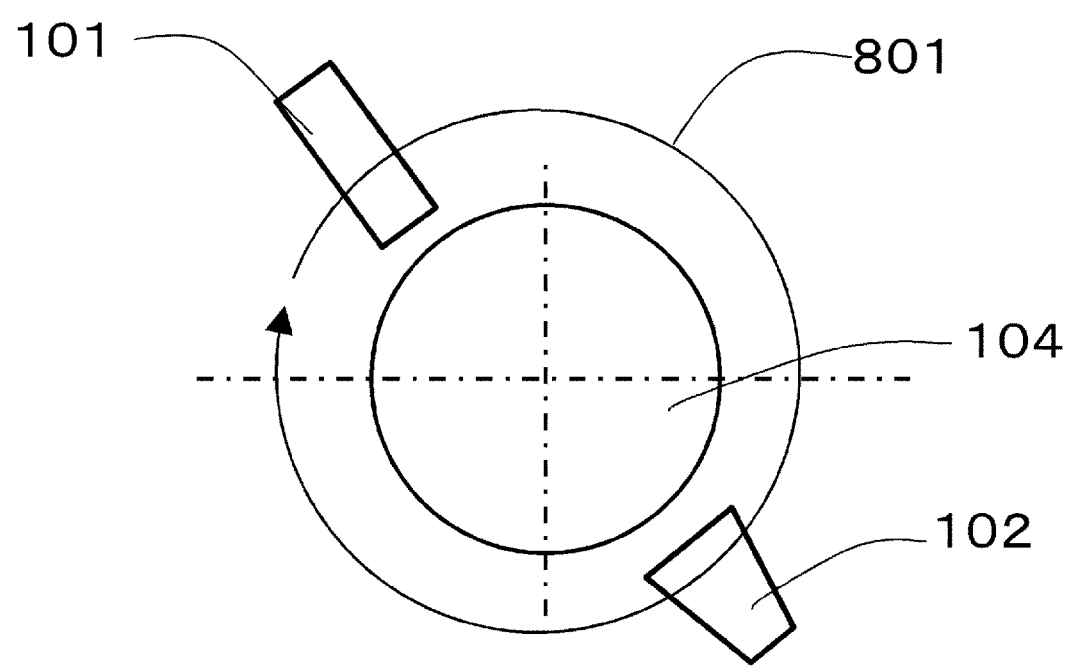

FIG. 11 is a diagram of an ultrasonic diagnostic apparatus according to the third embodiment of the present invention, and shows the configuration of parts around an object. FIGS. 11A and 11B are diagrams of the object sagging, as viewed from one side and from above respectively.

An object (a breast in the present invention) 104 is allowed to sag. A probe 101 and a light emission unit 102 are installed in opposite positions with the object 104 between them. The probe 101 and light emission unit 102 are moved so as to acquire data within a data acquisition range.

The probe 101 moves in a circular direction 801, as a main scan direction, around an axis 803 through the object, and moves in a direction 802, as a sub-scan direction, substantially perpendicular to the main scan direction. In the present embodiment, the data acquisition range is a range obtained by moving in a sub-scan direction a plane in which the probe 101 is rotated 360° around the axis 803.

In order to receive photoacoustic waves generated in the object 104, a medium (e.g. water or caster oil) that transmits ultrasonic waves is injected between the probe 101 and subject 104.

Since the outline of the system and the flow of data processing are the same as those in the first embodiment, explanation thereof is omitted, and acquisition of photo acoustic signals by using a plurality of wavelengths will be explained with reference to the drawings.

Figure 12:
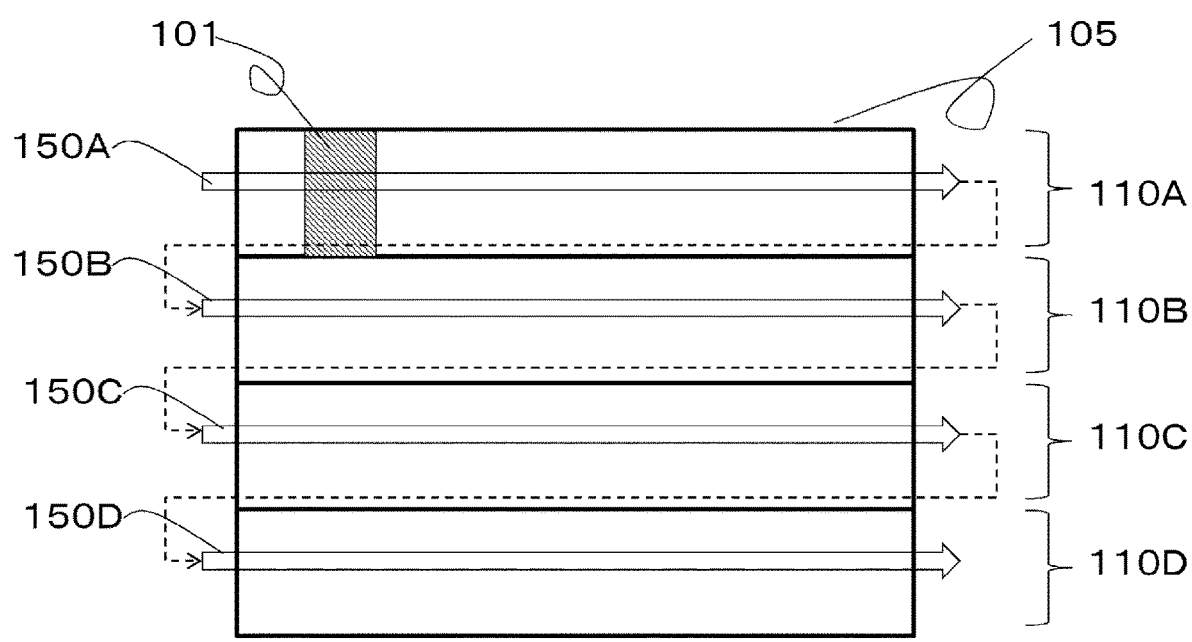
FIG. 12 is a diagram schematically showing probe movement according to the third embodiment.

FIG. 12 illustrates a data acquiring operation that is performed in the present embodiment. The main scan direction is a circular direction around the axis 803, as described above. However, here, a two-dimensional drawing in which circular direction are developed in a plane is used for ease of explanation. That is to say, the right and left ends of the data acquisition range 105 in FIG. 12 are continuous with each other.

First, the probe 101 is rotated 360° (indicated by the hollow-line arrow in 150A) around the axis 803. During movement in this main scan direction, wavelength switching is carried out. In the present embodiment, wavelength is switched for each pulse. That is, switching takes place in the following order: λ1, λ2, λ1, λ2, and so on. In order to speedily change the wavelength of pulsed light generated by laser light source, two lasers may be used alternately.

Such an operation makes it possible to acquire photoacoustic signals corresponding to pulsed light of wavelengths λ1 and λ2 within the partial data acquisition range 110A. At the time that the probe 101 has been rotated 360° around the axis 803, the probe 101 is shifted to the sub-scan direction, and the probe 101 is again rotated 360° (the hollow-line arrow in 150B) around the axis 803, thereby acquiring data within a partial data acquisition range 110B. Data are acquired for partial data acquisition ranges 110C and 110D in a similar manner.

While movement in the main scan direction is carried out in such a manner, control is exerted to switch the wavelength of pulsed light generated by laser light source, and the data is acquired from the data acquisition range.

Figure 13:
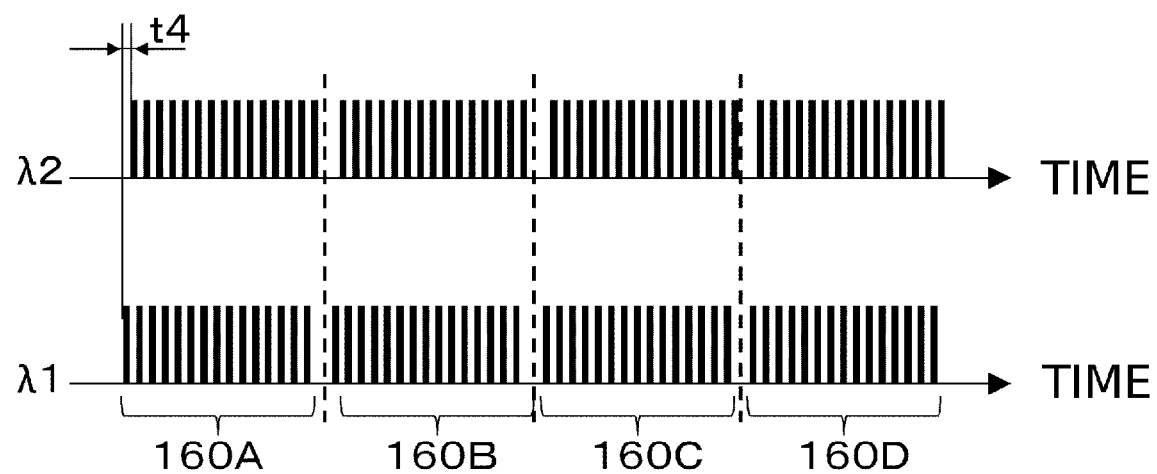
FIG. 13 is a time chart showing data acquisition according to the third embodiment.

FIG. 13 is a time chart showing emitted wavelengths. The range of 160A schematically shows the period for which wavelength switching is carried out for each pulse and each photoacoustic signal corresponding to pulsed light of wavelength λ1 and each photoacoustic signal corresponding to pulsed light of wavelength λ2 are acquired within a partial data acquisition range 110A. Similarly, the ranges 160B, 160C, and 160D correspond to 110B, 110C, and 110D.

In probe scanning in the present embodiment, the acquisition interval between photoacoustic signals corresponding to the wavelengths λ1 and λ2 within the same partial data acquisition range is indicated by t4. This acquisition interval is notably shorter compared to that where, after photoacoustic signals corresponding to emissions of pulsed light of wavelength λ1 are acquired within the entire data acquisition range, photoacoustic signals corresponding to emissions of pulsed light of the wavelength λ2 are acquired.

According to the present embodiment, since wavelength switching is carried out during movement in the main scan direction, acquisition interval between photoacoustic signals corresponding to different wavelengths can be further shortened within the same partial data acquisition range. That is, error due to movement of an object, which accompanies the passage of time, can be further reduced.

Therefore, by use of data reconstructed from photoacoustic signals obtained from the plurality of wavelengths (λ1 and λ2), error resulting from displacement is further reduced when oxygen saturation and so on are calculated in the multi-wavelength composing unit. Accordingly, a more reliable, highly accurate image can be composed.

In the present embodiment, while the probe is continuously moved in the ma in scan direction, wavelength switching and acquisition of photoacoustic signals are carried out. Specifically, in movement in the main scan direction, the probe is not stopped at each reception position but is moved at almost constant speed. Therefore, as shown in FIG. 13, the acquisition position (reception position) of a photoacoustic signal when light of wavelength λ1 is emitted and that when light of wavelength λ2 is emitted do not coincide exactly. However, if the frequency of pulsed light is sufficiently high, processing can substantially proceed without taking differences between acquisition positions into consideration. Additionally, even if the acquisition position of a photoacoustic signal corresponding to each light pulse is displaced, image data in a fixed area within each partial data acquisition range is calculated in the reconstruction block 206. Therefore, image reconstruction corresponding to the same position can be achieved.

Alternatively, the probe may be stopped at one position on an object, in which case, photoacoustic signals are received by using light of wavelengths λ1 and λ2, and then the probe may be moved in the next position. In this case, photoacoustic signals with almost no time difference can be acquired at the same reception position with respect to the object.

In the present embodiment, the main scan direction is specified as a circular direction around the axis. However, even where the probe is used for two-dimensional scanning, as in spatial arrangement of the first embodiment, the advantageous effects of the present invention can be obtained.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-183574, filed on Aug. 25, 2011, which is hereby incorporated by reference herein in its entirety.

The invention claimed is:

1. An object information acquiring method by using a spectroscopic photoacoustic imaging apparatus including a multi-wavelength light source, a transducer, and a scanning unit of the transducer, the method comprising:
dividing a whole region for which object information is to be acquired into a plurality of segmented regions to be scanned at least a plurality of times in association with a plurality of wavelengths of a plurality of pulsed lights from the multi-wavelength light source;
scheduling a scanning sequence including information in association with a scanning order of the plurality of segmented regions and a switching timing of a wavelength of an irradiation pulsed light from the multi-wavelength light source;
moving the transducer with respect to an object to scan the selected segmented region during a period of time for light irradiation with the pulsed light in the selected wavelength based on the scanning sequence;
receiving an acoustic wave signal with the transducer which is configured to obtain an electrical signal in association with the acoustic wave signal;
and
processing the electrical signal to acquire object information in association with the plurality of wavelengths of a plurality of pulsed lights,
wherein moving the transducer is performed such that the wavelength of the pulsed light is to be switched in a period of time when the transducer scans within one of the segmented regions or in a period of time when the transducer moves inter-region between the segmented regions.

2. The object information acquiring method according to claim 1, wherein moving the transducer comprises moving the transducer in a main scan direction in one of the segmented regions while the transducer receives the acoustic wave, and moving the transducer in a sub scan direction intersecting the main scan direction in the inter-region between the segmented regions.

3. The object information acquiring method according to claim 1, wherein moving the transducer comprises performing a first scan step and a second scan step after the first scan step within one of the segmented regions, and
wherein the wavelength of the pulsed light is switched in an inter period after the first scan step and before the second scan step.

4. The object information acquiring method according to claim 3, wherein moving the transducer further comprises performing a third scan step and a fourth scan step after the third scan step within a next segmented region different from the one segmented region in a position, and
wherein the wavelength of the pulsed light is switched in an inter period after the second scan step and before the third scan step.

5. The object information acquiring method according to claim 2, wherein the data acquisition region is divided into the plurality of segmented regions arranged in the sub scan direction.

6. The object information acquiring method according to claim 2, wherein the data acquisition region is divided into the plurality of segmented regions arranged in the main scan direction.

7. The object information acquiring method according to claim 1, wherein the wavelength of the pulsed light is switched each time the pulsed light is emitted.

8. The object information acquiring method according to claim 1, wherein processing the electrical signal comprises acquiring first object information in association with the pulsed light in a first wavelength, acquiring second object information in association with the pulsed light in a second wavelength, and storing the first object information and the second object information in a storage unit.

9. The object information acquiring method according to claim 1, wherein the object information includes at least one of initial acoustic pressure of the acoustic wave, density of light energy absorbed, absorption coefficient, and information reflecting the concentrations of substances.

10. The object information acquiring method according to claim 1, wherein a scan of the data acquisition region while irradiating with the pulsed light in a first wavelength and a scan of the data acquisition region while irradiating with the pulsed light in a second wavelength is completed in a 2T period of time, and
wherein a first switching timing of the pulsed light is earlier than T and a second switching timing of the pulsed light is earlier than 2T.

11. An object information acquiring method by using a spectroscopic photoacoustic imaging apparatus including a multi-wavelength light source, a transducer, and a scanning unit of the transducer, the method comprising:
- dividing a whole region for which object information is to be acquired into a plurality of segmented regions to be scanned at least a plurality of times in association with a plurality of wavelengths of a plurality of pulsed lights from the multi-wavelength light source;
- scheduling a scanning sequence including information in association with a scanning order of the plurality of segmented regions and a switching timing of a wavelength of an irradiation pulsed light from the multi-wavelength light source;
- moving the transducer with respect to an object to scan the selected segmented region during a period of time for light irradiation with the pulsed light in the selected wavelength based on the scanning sequence;
- receiving an acoustic wave signal with the transducer which is configured to obtain an electrical signal in association with the acoustic wave signal; and
- processing the electrical signal to acquire object information in association with the plurality of wavelengths of a plurality of pulsed lights,
- wherein a scan of the data acquisition region while irradiating with the pulsed light in a first wavelength and a scan of the data acquisition region while irradiating with the pulsed light in a second wavelength is completed in a 2T period of time, and
- wherein a first switching timing of the pulsed light is earlier than T and a second switching timing of the pulsed light is earlier than 2T.

12. The object information acquiring method according to claim 1, wherein the dividing the whole region to be acquired is performed based on an order from a user.

* * * * *